(12) United States Patent
Njoroge et al.

(10) Patent No.: US 6,706,883 B1
(45) Date of Patent: Mar. 16, 2004

(54) PROCESS FOR PRODUCING (8-CHLORO-3, 10-DIBROMO-6,11-DIHYDRO-5H-BENZO[5,6] CYCLOHEPTA[1,2-B]PYRIDIN-11-YL)-1-PIPERDINE

(75) Inventors: F. George Njoroge, Union, NJ (US); Bancha Vibulbhan, Kenilworth, NJ (US); Viyyoor M. Girijavallabhan, Parsippany, NJ (US)

(73) Assignee: Schering Corporation, Kenilworth, NJ (US)

(*) Notice: Subject to any disclaimer, the term of this patent is extended or adjusted under 35 U.S.C. 154(b) by 435 days.

(21) Appl. No.: 09/345,966

(22) Filed: Jul. 1, 1999

Related U.S. Application Data
(60) Provisional application No. 60/091,585, filed on Jul. 2, 1998.

(51) Int. Cl.[7] ............................................. C07D 401/04
(52) U.S. Cl. ....................................................... 546/293
(58) Field of Search ............................................ 546/93

(56) References Cited

U.S. PATENT DOCUMENTS 4,659,671 A * 4/1987 Klibanov ..................... 435/280
5,200,555 A * 4/1993 Kessels ....................... 562/401

FOREIGN PATENT DOCUMENTS

WO          97/23478      *  7/1997
WO          WO 98/58073      12/1998

* cited by examiner

*Primary Examiner*—Evelyn Mei Huang
(74) *Attorney, Agent, or Firm*—Henry C. Jeanette

(57) ABSTRACT

A process for producing compounds of the formula:

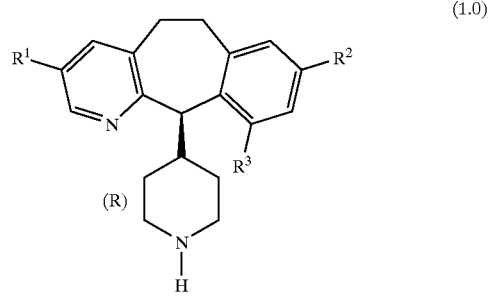

(1.0)

is disclosed. The compound of formula 1.0 is produced by:

(1) separating the atropisomers of

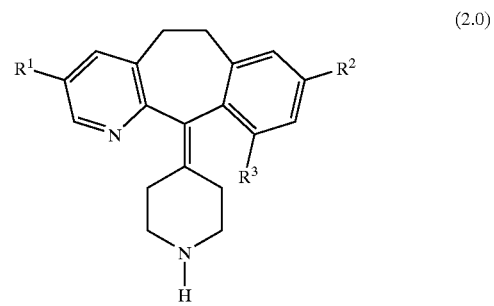

(2.0)

to obtain the atropisomers

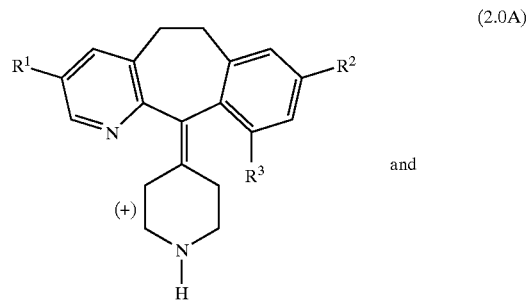

(2.0A) and (2.0B)

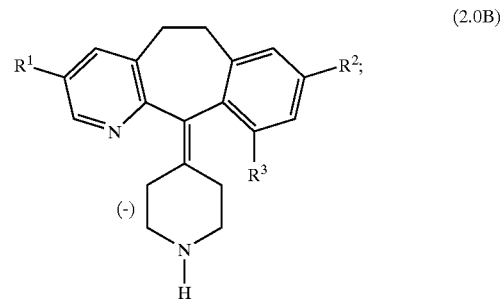

(2) heating the atropisomer of formula 2.0B at a suitable temperature in a suitable solvent to obtain a mixture of atropisomers of formulas 2.0A and 2.0B; (3) separating the atropisomers of formulas 2.0A and 2.0B of step (2); and (4) reducing the atropisomer of formula 2.0A to obtain a compound of formula 1.0. Preferably, $R^1$ is Br, $R^2$ is Cl and $R^3$ is Br.

Also disclosed is the (+)-atropisomer of formula 2.0 wherein $R^1$ is Br, $R^2$ is Cl and $R^3$ is Br.

15 Claims, No Drawings

US 6,706,883 B1

PROCESS FOR PRODUCING (8-CHLORO-3, 10-DIBROMO-6,11-DIHYDRO-5H-BENZO[5,6] CYCLOHEPTA[1,2-B]PYRIDIN-11-YL)-1-PIPERDINE

REFERENCE TO RELATED APPLICATIONS

This application claims the benefit of U.S. Provisional Application Serial No. 60/091,585 filed Jul. 2, 1998.

BACKGROUND OF THE INVENTION

Tricyclic compounds useful as inhibitors of farnesyl protein transferase (FPT) are known in the art.

WO97/23478 published Jul. 3, 1997 discloses the preparation of an intermediate useful in the preparation of FPT inhibitors. The intermediate

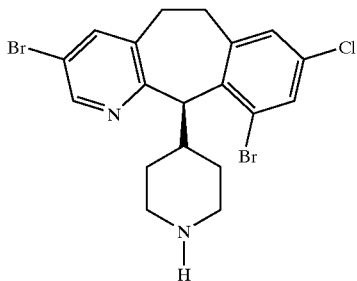

is prepared by reacting

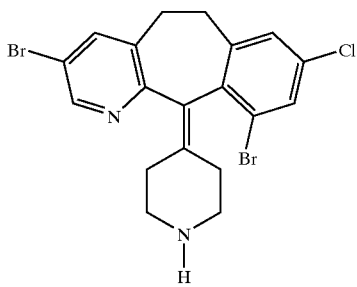

with diisobutylaluminum hydride followed by separation of the racemic mixture using a chiralpak AD column.

Processes which provide improved yields of the above intermediate would be a welcome contribution to the art. This invention provides such a process.

SUMMARY OF THE INVENTION

This invention provides a process for producing a compound of the formula:

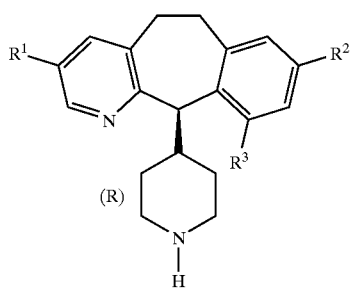
(1.0)

comprising:

(1) separating the atropisomers of

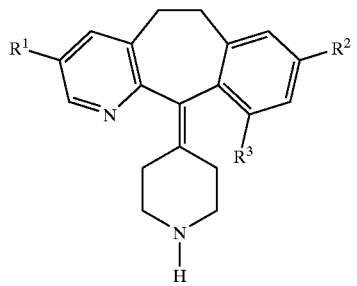
(2.0)

to obtain the atropisomers

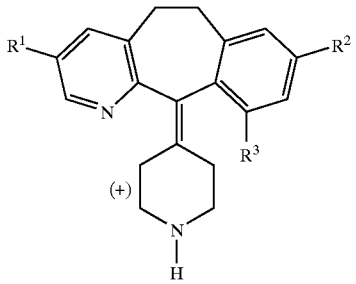
(2.0A)

and

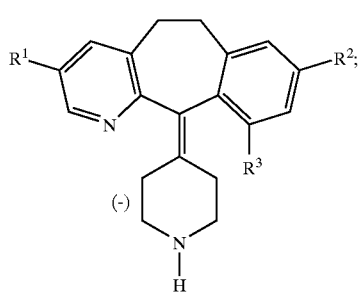
(2.0B)

(2) heating the atropisomer of formula 2.0B at a suitable temperature in a suitable solvent to obtain a mixture of atropisomers of formulas 2.0A and 2.0B;

(3) separating the atropisomers of formulas 2.0A and 2.0B of step (2); and (4) reducing the atropisomer of formula 2.0A to obtain a compound of formula 1.0;

wherein:

$R^1$, $R^2$, and $R^3$ are independently selected from halogen (i.e., Cl, Br, or I), $C_1$ to $C_6$ alkyl or —$OR^4$ wherein $R^4$ is a $C_1$ to $C_6$ alkyl.

Preferably, $R^1$ is Br, $R^2$ is Cl and $R^3$ is Br—i.e., preferably this invention provides a process for producing a compound of the formula:

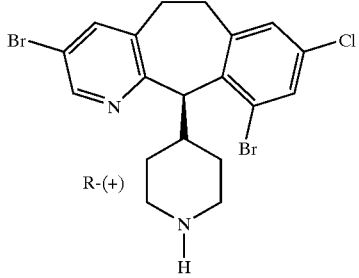

comprising:
(1) separating the atropisomers of

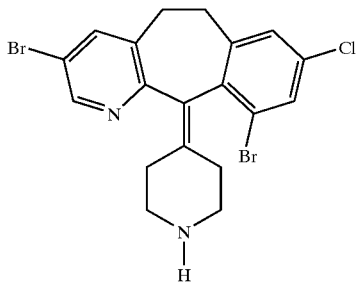

to obtain the atropisomers

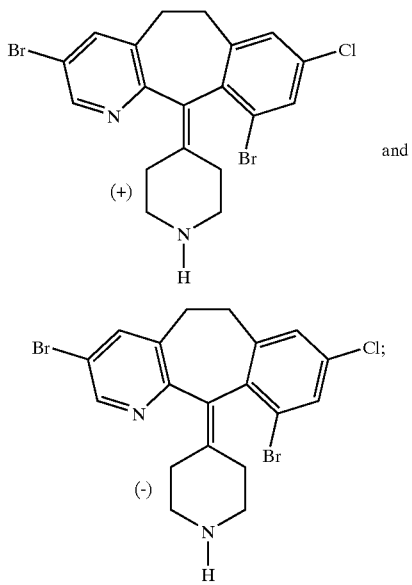

(2) heating the atropisomer of formula 2.1B at a suitable temperature in a suitable solvent to obtain a mixture of atropisomers of formulas 2.1A and 2.B;
(3) separating the atropisomers of formulas 2.1A and 2.1B of step (2); and
(4) reducing the atropisomer of formula 2.1A to obtain a compound of formula 1.1.

DETAILED DESCRIPTION OF THE INVENTION

The process of this invention provides the compound of formula 1.0 (preferably 1.1) as the specific (R)-isomer—i.e., no racemic mixture (based on C-11) is produced in the reduction step. Those skilled in the art will appreciate that C-11 position in the tricyclic ring is

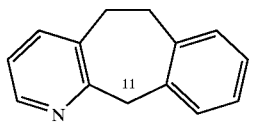

The intermediate compound of formula 1.1 is useful in the preparation of FPT inhibitors disclosed, for example, in WO97/23478. Thus, the compound of formula 1.1 is useful in the preparation of:

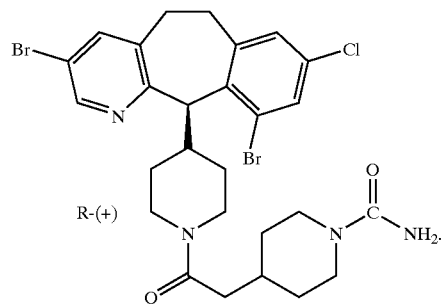

In the process of this invention atropisomer 2.0A obtained in step 1 above can be reduced while additional atropisomer 2.0A is being obtained in steps 2 and 3 above. Thus, atropisomer 2.0A from step 1 above can be reduced as soon as it is obtained. Alternatively, atropisomer 2.0A obtained from step 1 above can be combined with atropisomer 2.0A obtained from steps 2 and 3 above, and the total amount of atropisomer 2.0A can be reduced at one time. Steps 2 and 3 above can be repeated to obtain additional atropisomer 2.0A from atropisomer 2.0B.

Preferably, formula 2.0 is separated, in step 1, into its atropisomers using HPLC and a suitable column (i.e., a column that will provide the desired degree of separation in a reasonable amount of time). Preferably, for separating compound 2.1, the column is packed with amylose tris(3, 5-dimethylphenyl carbamate) coated on a 10 micron silica gel. This column is commercially available under the tradename Chiralpak AD.

A suitable elution solvent is used to obtain separation of the atropisomers. A suitable solvent is one which provides the desired degree of polarity to sufficiently separate the isomers in a reasonable amount of time. For example, the solvent can comprise: (1) a low boiling alcohol (e.g., isopropanol, methanol, ethanol, mixtures thereof, or the like); (2) a low boiling organic co-solvent (e.g., hexane, pentane, heptane, mixtures thereof, or the like); and (3) an organic base (e.g., diethylamine, diisopropylamine, triethylamine, mixtures thereof, or the like). The solvent, for example, can comprise from about 15 to about 35% alcohol, and about 40 to about 85% organic co-solvent, and about 0.1 to about 1% base, such that the total amount equals 100%v/v. For example, the elution solvent can comprise about 15 to about 35% isopropyl alcohol, and about 40 to about 85% hexane, and about 0.1 to about 1% diethylamine such that the total amount equals 100%v/v. Preferably, for compound 2.1, the elution solvent comprises 35% isopropyl alcohol and 0.2% diethylamine in hexane.

To convert atropisomer 2.0B to a mixture of atropisomers 2.0A and 2.0B, atropisomer 2.0B is heated at a suitable temperature in a suitable organic solvent. For example, atropisomer 2.0B can be heated to 100 to 200° C. in an appropriate high boiling solvent. Generally, atropisomer 2.0B is heated to reflux in the solvent. Examples of solvents include dimethyl formamide, toluene, and and 1,2-dichlorobenzene. Preferably, atropisomer 2.1B is heated in 1,2-dichlorobenzene at a temperature of about 150° C.

The atropisomer of formula 2.0A is reduced using a suitable reducing agent. Preferably, diisobutylaluminum hydride is used. The reduction is carried out using conditions well known to those skilled in the art. For example, atropisomer 2.0A can be dissolved in a suitable organic solvent (e.g., toluene) to which a suitable amount of diisobutylaluminum hydride is added to effectively reduce 2.0A. The solution is then refluxed under nitrogen. The desired product can then be isolated by known separation procedures.

This invention is exemplified by the following example, which should not be construed to limit the scope of the disclosure.

EXAMPLE 1

Step 1

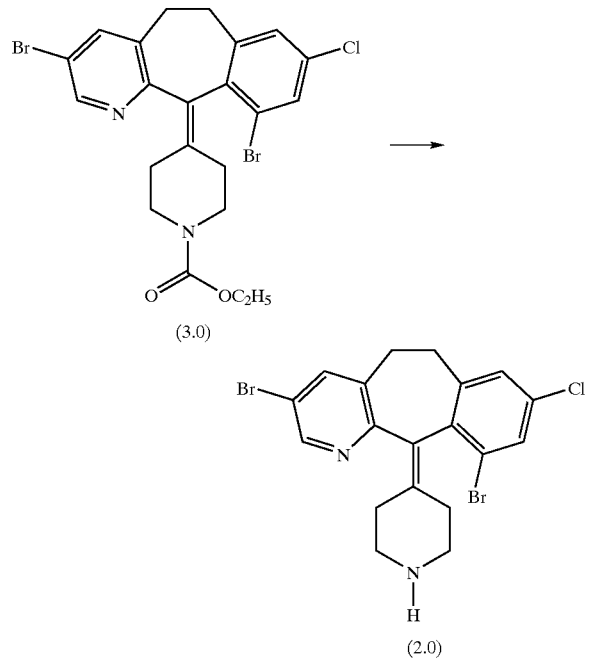

To 8 mL of concentrated HCl was added the compound of formula 3.0 (0.7 g, 1.4 mmol). The reaction mixture was refluxed for 16 hours. The reaction mixture was then cooled, poured into an ice bath and basified to pH 10 with aqueous 50% NaOH. The aqueous phase was extracted with $CH_2Cl_2$. Concentration of the organic phase afforded 0.59 g of the compound of formula 2.0. mp=123.9–124.2° C. $^1$H NMR (200 MHz, $CDCl_3$) δ1.99–3.60 (m, 13H), 7.20 (s, 1H), 7.50 (s, 1H), 7.51 (s, 1H), 8.50 (s, 1H). MS m/z (rel intens) 688 (100, MH+).

Step 2

The compound of formula 2.0 obtained in Step 1 was loaded on a Chiracel AD column (in HPLC) and eluted with 35% isopropyl alcohol-hexane-containing 0.2% diethylamine to give 4.28 g of atropisomer of formula 2.0A (eluting at retention time 13.04 minutes) and 3.56 g of atropisomer 2.0B (eluting at retention time 51.18 minutes).

Physical chemical data for isomer 2.0A: mp=92–93° C., MS m/z 470 (MH+); $[\alpha]_D^{25}$=+166.30° (10.02 mg/2 mL MeOH).

Physical chemical data for isomer 2.0B: mp=96–97° C., MS m/z 470 (MH+); $[\alpha]_D^{25}$=−190.2° (9.62 mg/2 mL MeOH).

Step 3

To a solution of atropisomer 2.0A (0.38 g, 0.8 mmol) dissolved in toluene (10 mL) was added 0.8 mL (1 eq) of diisobutylaluminum hydride (1 M solution in toluene). the solution was brought to reflux under nitrogen and an additional 1.04 mL (1.3 eq) of 1 M diisobutylaluminum hydride in toluene was added dropwise over 15 minutes. the solution was cooled in an ice-water bath, then mixed with 1 M hydrochloric acid (10 mL). The organic phase was discarded and the aqueous phase was washed with dichloromethane which was also discarded. The aqueous phase was basified with 1 N aqueous sodium hydroxide., extracted with dichloromethane and dried over anhydrous $MgSO_4$. Filtration and concentration in vacuo afforded 0.27 g of compound 1.0 as a white solid. mp=95–96° C. MS (Cl) m/z 469 (MH+). $[\alpha]_D^{25}$=+51.9° (7.71 mg/2 mL MeOH). $^1$H NMR (200 MHz, $CDCl_3$) δ(ppm) 1.16–1.83 (m, 5H), 2.16–2.57 (m, 3H), 2.69–3.17 (m, 1H), 3.65 (m, 1H), 4.91 (d, 1H, J=10 Hz), 7.13 (d, 1H, J=2 Hz), 7.50 (d, 1H, J=2 Hz), 7.54 (d, 1H, J=2 Hz), 8.45 (d, 1H, J=2 Hz).

Step 4

Atropisomer 2.0B (0.25g) was converted to atropisomer by heating in 4 mL of 1,2-dichlorobenzene at 150° C. After 7 days 45% of atropisomer was converted to atropisomer 2.0A.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for producing a compound of the formula:

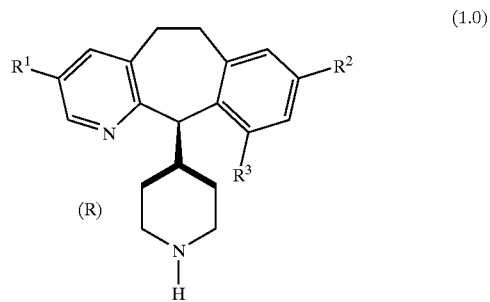

comprising:

I. (1) separating the atropisomers of

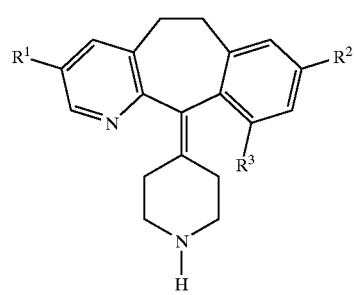
(2.0)

by HPLC to obtain the atropisomers

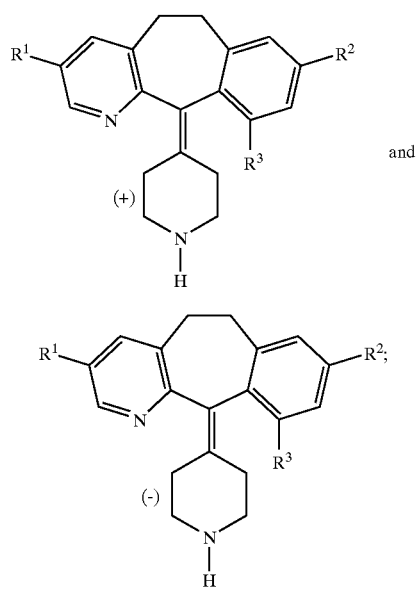
(2.0A)
and
(2.0B)

(2) heating the atropisomer of formula 2.0B at a temperature of 100 to 200° C., in a solvent selected from dimethyl formamide, toluene or 1,2-dichlorobenzene, to obtain a mixture of atropisomers of formulas 2.0A and 2.0B;

(3) separating the atropisomers of formulas 2.0A and 2.0B of step (2) by HPLC; and (4) reducing the atropisomer of formula 2.0A to obtain a compound of formula 1.0; or II. (1) separating the atropisomers of

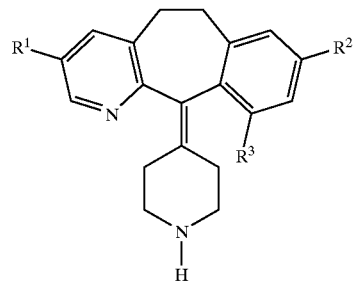
(2.0)

by HPLC to obtain the atropisomers

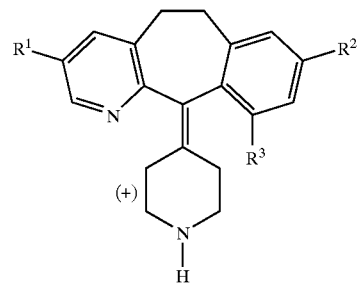
(2.0A)
and

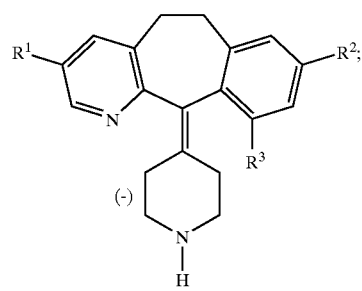
(2.0B);

(2) reducing the atropisomer of formula 2.0A to obtain a compound of formula 1.0;

(3) heating the atropisomer of formula 2.0B at a temperature of 100 to 200° C., in a solvent selected from dimethyl formamide, toluene or 1,2-dichlorobenzene, to obtain a mixture of atropisomers of formulas 2.0A and 2.0B;

(4) separating the atropisomers of formulas 2.0A and 2.0B of step (2) by HPLC; and (5) reducing the atropisomer of formula 2.0A obtained in Step (4) to obtain a compound of formula 1.0;

wherein:

$R^1$, $R^2$, and $R^3$ are independently selected from halogen, $C_1$ to $C_6$ alkyl or —$OR^4$ wherein $R^4$ is a $C_1$ to $C_6$ alkyl.

2. A process for producing a compound of the formula:

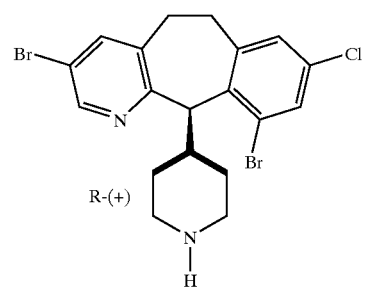
(1.1)

comprising:

(1) separating the atropisomers of

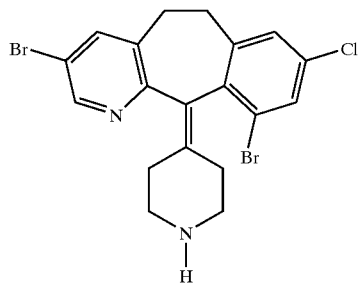
(2.1)

by HPLC to obtain the atropisomers

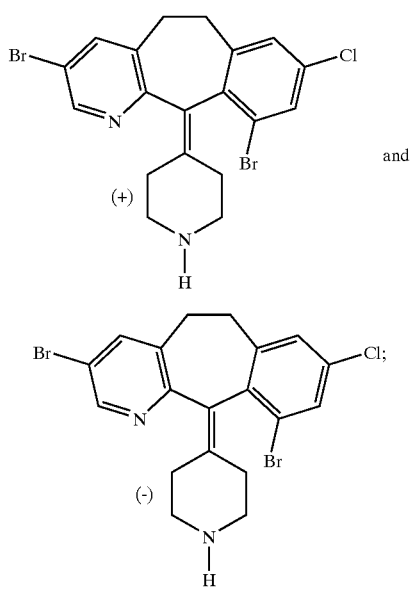

(2) heating the atropisomer of formula 2.1B at a temperature of 100 to 200° C., in a solvent selected from dimethyl formamide, toluene or 1,2-dichlorobenzene, to obtain a mixture of atropisomers of formulas 2.1A and 2.1B;
(3) separating the atropisomers of formulas 2.1A and 2.1B of step (2) by HPLC;
(4) reducing the atropisomer of formula 2.1A to obtain a compound of formula 1.1; and
(5) wherein the HPLC column used in steps (1) and (3) comprises amylose tris(3,5-dimethylphenyl carbamate) coated on a 10 micron silica gel substrate, and an elution solvent is used comprising 15 to about 35% isopropyl alcohol, and about 40 to about 85% hexane, and about 0.1 to about 1% diethylamine such that the total amount equals 100%v/v.

3. The process of claim 2 wherein elution solvent comprises about 35%v/v isopropyl alcohol and about 0.2%v/v diethylamine in hexane.

4. The process of claim 2 wherein atropisomer 2.1B is heated in 1,2-dichlorobenzene to obtain the mixture of atropisomers 2.1A and 2.1B.

5. The process of claim 4 wherein atropisomer 2.1B is heated at about 150° C.

6. The process of claim 2 wherein atropisomer 2.1A is reduced using diisobutylaluminum hydride.

7. The process of claim 2 wherein: (a) atropisomer 2.1B is heated at about 150° C. in 1,2-dichlorobenzene to obtain the mixture of atropisomers 2.1A and 2.1B; and (b) atropisomer 2.1A is reduced using diisobutylaluminum hydride.

8. The process of claim 7 wherein elution solvent comprises about 35%v/v isopropyl alcohol and about 0.2%v/v diethylamine in hexane.

9. A process for producing a compound of the formula:

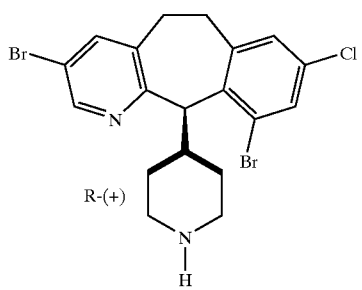
(1.1)

comprising:
(1) separating the atropisomers of

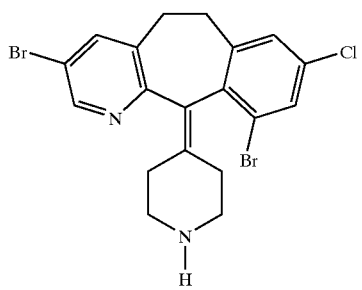
(2.1)

by HPLC to obtain the atropisomers

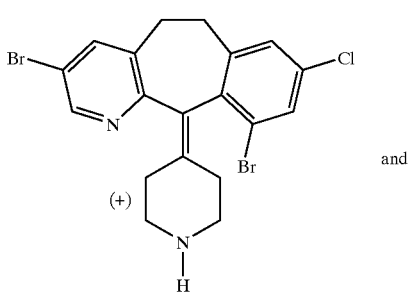
(2.1A)

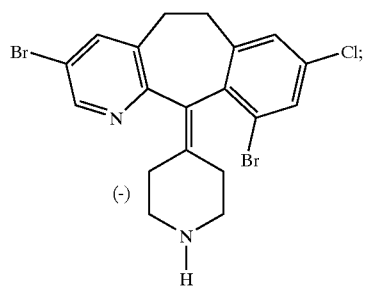
(2.1B)

(2) reducing the atropisomer of formula 2.1A to obtain a compound of formula 1.1;
(3) heating the atropisomer of formula 2.1B at a temperature of 100 to 200° C., in a solvent selected from dimethyl formamide, toluene or 1,2-dichlorobenzene, to obtain a mixture of atropisomers of formulas 2.1A and 2.1B;

(4) separating the atropisomers of formulas 2.1A and 2.1B of step (2) by HPLC;

(5) reducing the atropisomer of formula 2.1A obtained in Step (4) to obtain a compound of formula 1.1; and (6) wherein the HPLC column used in steps (1) and (4) comprises amylose tris(3,5-dimethylphenyl carbamate) coated on a 10 micron silica gel substrate, and an elution solvent is used comprising 15 to about 35% isopropyl alcohol, and about 40 to about 85% hexane, and about 0.1 to about 1% diethylamine such that the total amount equals 100%v/v.

10. The process of claim 9 wherein said elution solvent comprises about 35%v/v isopropyl alcohol and about 0.2%v/v diethylamine in hexane.

11. The process of claim 9 wherein atropisomer 2.1B is heated in 1,2-dichlorobenzene to obtain the mixture of atropisomers 2.1A and 2.1B.

12. The process of claim 11 wherein atropisomer 2.1B is heated at about 150° C.

13. The process of claim 9 wherein atropisomer 2.1A is reduced using diisobutylaluminum hydride.

14. The process of claim 9 wherein: (a) atropisomer 2.1B is heated at about 150° C. in 1,2-dichlorobenzene to obtain the mixture of atropisomers 2.1A and 2.1B; and (b) atropisomer 2.1A is reduced using diisobutylaluminum hydride.

15. The process of claim 14 wherein elution solvent comprises about 35%v/v isopropyl alcohol and about 0.2%v/v diethylamine in hexane.

* * * * *